United States Patent
Xu

(10) Patent No.: US 10,577,299 B2
(45) Date of Patent: Mar. 3, 2020

(54) METHODS FOR USING MACROPOROUS INERT MATERIALS IN MONOMER PRODUCTION

(71) Applicant: Rohm and Haas Company, Collegeville, PA (US)

(72) Inventor: Jinsuo Xu, Berwyn, PA (US)

(73) Assignee: Rohm and Haas Company, Collegeville, PA (US)

(*) Notice: Subject to any disclaimer, the term of this patent is extended or adjusted under 35 U.S.C. 154(b) by 0 days.

(21) Appl. No.: 16/092,094

(22) PCT Filed: Apr. 17, 2017

(86) PCT No.: PCT/US2017/027898
§ 371 (c)(1),
(2) Date: Oct. 8, 2018

(87) PCT Pub. No.: WO2017/184496
PCT Pub. Date: Oct. 26, 2017

(65) Prior Publication Data
US 2019/0112252 A1    Apr. 18, 2019

Related U.S. Application Data

(60) Provisional application No. 62/325,715, filed on Apr. 21, 2016.

(51) Int. Cl.
| | | |
|---|---|---|
| *C07C 51/25* | (2006.01) | |
| *C07C 47/22* | (2006.01) | |
| *C07C 57/04* | (2006.01) | |
| *C07C 45/33* | (2006.01) | |
| *B01J 23/31* | (2006.01) | |
| *C07C 45/34* | (2006.01) | |

(52) U.S. Cl.
CPC ............. *C07C 51/252* (2013.01); *B01J 23/31* (2013.01); *C07C 45/33* (2013.01); *C07C 45/34* (2013.01); *C07C 47/22* (2013.01); *C07C 57/04* (2013.01)

(58) Field of Classification Search
CPC .......... B01J 23/31; C07C 45/33; C07C 45/34; C07C 47/22; C07C 51/252; C07C 57/04
See application file for complete search history.

(56) References Cited

U.S. PATENT DOCUMENTS

| | | | |
|---|---|---|---|
| 4,147,885 A | | 4/1979 | Shimizu et al. |
| 5,087,744 A | | 2/1992 | Krabetz et al. |
| 5,442,108 A | | 8/1995 | Kawajiri et al. |
| 5,532,199 A | | 7/1996 | Watanabe et al. |
| 5,959,143 A | | 9/1999 | Sugi et al. |
| 6,069,271 A | * | 5/2000 | Tanimoto ................ B01J 8/067 422/198 |
| 6,545,178 B1 | | 4/2003 | Tanimoto et al. |
| 6,762,148 B2 | | 7/2004 | Ohishi et al. |
| 6,994,833 B1 | | 2/2006 | Nishimura et al. |
| 7,731,919 B2 | | 6/2010 | Fukumoto |
| 8,603,423 B2 | * | 12/2013 | Andersen ................ B01J 23/30 423/213.2 |
| 2004/0192965 A1 | * | 9/2004 | Petzoldt ................ C07C 51/252 562/534 |
| 2004/0242926 A1 | | 12/2004 | Dieterle et al. |
| 2013/0274508 A1 | | 10/2013 | DeCourcy et al. |

FOREIGN PATENT DOCUMENTS

| | | |
|---|---|---|
| WO | 2008136857 | 11/2008 |
| WO | 2013052421 | 4/2013 |

OTHER PUBLICATIONS

H.L. Ritter and L.C. Drake, "Pore size distribution in porous materials. Pressure porosimeter and determination of complete macropore-size distributions", Ind. Eng. Chem., vol. 17, 1945, p. 782-786.
S. Brunauer, P.H. Emmett, and E. Teller, "Adsorption of gases in multimolecular layers", Journal of American Chemical Society, vol. 60, 1938, p. 309-319.

* cited by examiner

*Primary Examiner* — Yevgeny Valenrod
*Assistant Examiner* — Blaine G Doletski
(74) *Attorney, Agent, or Firm* — Brian L. Mutschler

(57) ABSTRACT

The present invention provides methods for monomer production, for example, acrylic acid, wherein the methods comprise oxidizing one or more reactant gases, for example, propylene, in a fixed bed reactor, preferably, two fixed bed reactors, in the presence of oxygen and a mixed metal oxide catalyst to form an oxidized gaseous mixture and, at any point in the oxidizing, feeding or flowing the one or more reactant gases or the oxidized gaseous mixture through an inert macroporous material that has a pore volume of from 0.2 cm3/g to 2.0 cm3/g, a surface area of from 0.01 to 0.6 m2/g, and wherein from 30 to 98 wt. % of the total pore volume in the inert macroporous material has a pore diameter of at least 100 μm.

12 Claims, No Drawings

METHODS FOR USING MACROPOROUS INERT MATERIALS IN MONOMER PRODUCTION

The present invention relates to methods for preparing monomers, such as acrylic acid, which comprise oxidizing one or more reactant gases, such as propylene, in a fixed bed reactor in the presence of a mixed metal oxide catalyst to form an oxidized gaseous mixture and, at any point in the oxidizing, feeding the one or more reactant gases or the oxidized gaseous mixture through an inert macroporous material. More particularly, the methods comprise the oxidizing the one or more reactant gases or gaseous mixtures wherein the inert macroporous material has a pore volume of at least 0.2 cm$^3$/g or, preferably, at least 0.3 cm$^3$/g, the inert macroporous material has a surface area of 0.6 m$^2$/g or less or, preferably, 0.4 m$^2$/g or less, and at least 30%, or, preferably, at least 50% of the total pore volume in the inert macroporous material have a pore diameter of at least 100 μm.

Monomers, such as acrylic acid (AA), are produced via propylene oxidation over mixed metal oxide catalyst beds comprising two separate mixed metal oxide catalysts. Acrolein (ACR) intermediate is first produced over an first catalyst R1 by oxidation of propylene in the presence of steam to produce acrolein, and then is further oxidized to AA over a second catalyst R2. Shell and tube reactors are used with catalyst beds packed inside the tube, and heating media such as salt or a heat exchange fluid circulating between the tubes to control the reaction temperature. Tandem reactors and single reactor shell (SRS) reactors are known reactors for making AA; in tandem reactors, R1 and R2 are packed in two separate tubes, while in SRS reactors both R1 and R2 catalysts are packed in one tube.

Under normal use conditions, a pressure drop (DP) across the mixed metal oxide catalyst bed(s) will generally increase with time. The DP increase can be caused by the accumulation and deposition of particulate impurities, including but not limited to catalyst fines, sublimed molybdenum oxides, and high boiling point byproducts, such as phthalic acid, within the reactor, for example, at the bottom of a first tube reactor, at the interstage region between the tube containing R1 and the tube containing R2, top of the second tube reactor, or the bottom of second tube reactor. Accordingly, a larger DP increase corresponds with catalysts and reactor beds that have more accumulated particulate impurities. This higher DP over time will force the reactor to operate at a reduced rate or will result in a reduced yield of the desired product; and this DP increase will eventually render the catalysts, especially the second catalyst, unusable. Thus, when the reactor rate or yield drops to certain point, the reactor has to be shut down and packed with new catalysts. Such a shutdown is expensive and should be avoided.

Recent European Patent no. EP1714955 B1, to Nippon Shokubai Co., LTD. (NSCL), discloses gas-phase fixed bed catalytic oxidation wherein a solid acid is included in a reactor. The solid acid comprises metal oxides to suppress the deposition of catalyst inhibitors in the reactor and avoid a pressure drop in the reactor. However, the solid acid in the NSCL patent does not disclose preventing the formation of such inhibitors or capturing them to protect downstream catalyst or units from fouling.

The present inventors have sought to solve the problem of providing a catalytic oxidation process that reduce the impact and/or the amount of particulate contaminants formed in the oxidation process, and that enables one or more of prolonged catalyst lifetime, high reactant feed rates and high yields.

STATEMENT OF THE INVENTION

1. In accordance with the present invention methods for preparing monomers, such as acrylic acid or a monomer having an alpha, beta-unsaturated carboxlic acid group, comprise oxidizing one or more reactant gases, such as propylene, in a fixed bed reactor containing in at least one bed a mixed metal oxide catalyst in the presence of oxygen and the mixed metal oxide catalyst to form an oxidized gaseous mixture and, at any point in the oxidizing, feeding or flowing the one or more reactant gases or the oxidized gaseous mixture through an inert macroporous material that has a pore volume of from 0.2 cm$^3$/g to 2.0 cm$^3$/g, or, preferably, at least 0.3 cm$^3$/g, or, preferably, up to 1.6 cm$^3$/g, or, more preferably, at least 0.4 m$^2$/g, the inert macroporous material has a surface area of 0.6 m$^2$/g or less or as low as 0.01 m$^2$/g, or, preferably, 0.4 m$^2$/g or less, or, more preferably, 0.3 m$^2$/g or less, and wherein in the inert macroporous material from 30 to 98%, or, preferably, at least 50% of the total pore volume in the in the inert macroporous material have a pore diameter of at least 100 μm.

2. The methods in accordance with item 1 of the present invention, above, wherein the inert macroporous material is inert to the oxidizing of the one or more reactant gases to prepare the monomer.

3. The methods in accordance with item 2 of the present invention, wherein the first stage comprises oxidizing gaseous propylene in a first fixed bed reactor containing in at least one bed a mixed metal oxide catalyst having a bed temperature of from 280 to 450° C., or, preferably, from 320 to 400° C., in the presence of the first mixed metal oxide catalyst to generate a gaseous mixture comprising acrolein, wherein the mixed metal oxide catalyst contains Mo and Bi, and feeding the gaseous mixture to a second fixed bed reactor or a second stage of the first fixed bed reactor, the second fixed bed reactor or second stage of the first fixed bed reactor having a bed temperature of from 250 to 380° C., or, preferably, from 260 to 350° C. to produce a second product mixture comprising acrolein and acrylic acid.

4. The methods in accordance with any of items 1 to 3 of the present invention, above, wherein the oxidizing is conducted in two stages starting with a first stage in a first reactor containing in at least one bed a first catalyst R1, such as a mixed metal oxide catalyst, to generate a gaseous mixture and then a second stage in a second reactor or downstream in the first reactor containing in at least one bed a second catalyst R2, such as a mixed metal oxide catalyst, to generate a product comprising a monomer, such as a monomer having an alpha,beta-unsaturated carboxlic acid group.

5. The methods in accordance with any of items 1 to 4 of the present invention, above, wherein the one or more reactant gases comprises propylene which is oxidized to acrolein in a first stage and then to acrylic acid in a second stage, or one or more of isobutylene or tert-butanol which is oxidized to methacrolein in a first stage and then to methacrylic acid in a second stage.

6. The methods in accordance with any one of items 1 to 5 of the present invention, above wherein the inert macroporous material is chosen from a silicon oxide, an aluminum oxide, a silicon carbide, a zirconium oxide, a titanium oxide, a germanium oxide, metal silicates, organic polymers, porous metals, mixtures thereof and combinations thereof, preferably, a combination of silicon oxide and aluminum oxide.

7. The methods as in any one of items 1 to 6 of the present invention, wherein the one or more reactant gases is propylene gas that is oxidized in the oxidizing to an acrolein gaseous mixture by feeding the propylene gas to the upper stream of a first stage catalyst bed containing in the bed a solid first mixed metal oxide catalyst R1 at a first bed temperature, and then the resulting acrolein gaseous mixture is oxidized to an acrylic acid product by feeding the acrolein gaseous mixture to the upper stream of a second stage catalyst bed containing in the bed a solid second mixed metal oxide catalyst R2 at a second bed temperature, wherein the improvement comprises including the inert macroporous material in at least one of the upper stream of the first stage catalyst bed, the upper stream of the second stage catalyst bed, the bottom stream of the first stage catalyst bed, and the bottom stream of the second stage catalyst bed, preferably, the upper stream of the first catalyst bed, or, preferably, the upper stream of the second catalyst bed, or, more preferably, the upper streams of both the first catalyst bed and the second catalyst bed.

8. The methods as in item 7 of the present invention, above, wherein the first bed temperature ranges from 280 to 450° C. or, preferably, from 320 to 400° C., or the second bed temperature ranges from 250 to 380° C. or, preferably, from 260 to 350° C., or both.

9. The methods as in any one of items 1 to 8, above, wherein the oxidizing is vapor phase oxidation of propylene to acrolein and acrylic acid.

10. The methods as in any one of items 1 to 8, above, wherein the oxidizing is the vapor phase oxidation of isobutylene and/or tert-butanol to methacrolein and methacrylic acid.

11. The methods as in any one of items 1 to 10, above, wherein the mixed metal oxide catalyst used in the first stage reactor contains Mo and Bi.

12. The methods as in any one of items 1 or 3 to 11 of the present invention, wherein the one or more reactant gases are oxidized in a first tube reactor containing at least one first stage catalyst bed containing a solid first mixed metal oxide catalyst R1 at a first bed temperature to form a gaseous mixture and then the resulting gaseous mixture is oxidized to a monomer product by feeding the gaseous mixture to a second tube reactor containing at least one second stage catalyst bed containing a solid second mixed metal oxide catalyst R2, preferably, at the upper stream of the second tube reactor, wherein the at least one bed containing a second stage catalyst has a second bed temperature that is below the first bed temperature, such as from 250 to 380° C., wherein the improvement comprises including the macroporous material at the bottom of the first tube reactor, at the interstage region between the first tube reactor and the second tube reactor, at the top of the second tube reactor, or at the bottom of second tube reactor.

13. The methods as in item 12 of the present invention, above, wherein the first bed temperature ranges from 280 to 450° C., or, preferably, from 320 to 400° C., and the second bed temperature ranges from 250 to 380° C. or, preferably, from 260 to 350° C.

As used herein, "at least one" and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

The singular forms "a," "an," and "the" include plural referents unless the context clearly dictates otherwise.

All ranges recited are inclusive and combinable. For example, a recitation of a a pore volume of from 0.4 $cm^3/g$ to 0.98 $cm^3/g$, preferably at least 0.5 $cm^3/g$, means any or all of a pore volume of from 0.4 $cm^3/g$ to 0.98 $cm^3/g$, or from 0.4 $cm^3/g$ to 0.5 $cm^3/g$, or, preferably, from 0.5 to 0.98 $cm^3/g$.

Unless otherwise indicated, conditions of temperature and pressure are room temperature (22-24° C.) and standard pressure (760 mm/Hg or 101.3 Mpa), also referred to herein as "ambient conditions".

All phrases comprising parentheses denote either or both of the included parenthetical matter and its absence. For example, the phrase "(meth)acrylate" includes, in the alternative, acrylate and methacrylate.

As used herein, the term "heavy by-products" means compounds, such as benzoic acid, phthalic acid, isophthalic acid, terephthalic acid, and benzene-1,2,4-tricarboxylic acid, having a boiling point above 150° C. at a pressure of 1 atmosphere.

As used herein, the term "inert" refers to a macroporous material that generates a product comprising an equal or lower ratio of phthalic acid (PTA) to the total mass of acrolein and acrylic acid product than is generated in the absence of any macroporous material when oxidizing the same gaseous mixture (P1) comprising propylene, acrolein, and acrylic acid in the same way and under the same conditions absent any of the macroporous material. In one example, gaseous mixture P1 comprises from 0 to 0.5 mol. % propylene, from 0.1 to 1.0 mol. % acrylic acid, and from 1 to 10 mol. % acrolein. In the test, P1 is fed in the vapor phase at a pressure of from 101.3 to 152.0 KPa (1 to 1.5 atm) to a tubular fixed bed reactor having a total length (L) and a bed temperature of from 270 to 320° C., the reactor containing a cross-sectional bed of the macroporous material having a length L2 in which L2/L ranges from 0.61 to 0.73 through which P1 flows, and contacts the inert macroporous material for a contact time of at least 3 seconds so as to produce a product (P2) comprising acrolein and acrylic acid, followed by selectively condensing components of P2 under conditions sufficient to condense its components having a boiling point at a pressure of 101.3 KPa (1 atm) of at least 20° C., and then followed by analyzing the condensed components for phthalic acid, acrolein, and acrylic acid to determine the the ratio of the mass of phthalic acid in P2 to the total mass of acrolein and acrylic acid in P2. The remaining uncondensed vapor in P2 is analyzed for propylene, $O_2$, $N_2$, CO, and $CO_2$ content.

As used herein, the term "ppm" means part per million by weight.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth)acrylic acid" refers to either acrylic acid or methacrylic acid.

Unless otherwise indicated, as used herein, the term "pore volume" refers to the volume in $cm^3/g$ determined by mercury intrusion method (ref: H. L. Ritter and L. C. Drake, "Pore size distribution in porous materials. Pressure porosimeter and determination of complete macropore-size distributions", *Ind. Eng. Chem.*, *Vol.* 17, 1945, p. 782-786).

Unless otherwise indicated, as used herein, the term "surface area" refers to the amount in $m^2/g$ determined by nitrogen adsorption using BET method (ref: "Adsorption of gases in multimolecular layers", Journal of American Chemical Society, vol. 60, p. 309-319, 1938, by S. Brunauer, P. H. Emmett, and Edward Teller).

Unless otherwise indicated, as used herein, the term "pore diameter" is determined by mercury intrusion method (ref: H. L. Ritter and L. C. Drake, "Pore size distribution in porous materials. Pressure porosimeter and determination of complete macropore-size distributions", Ind. Eng. Chem., 17, 1945, p. 782-786). The portion of material having at least a specified pore diameter thereof refers to the value determined by volume percentage.

Gas phase reactors for use in the present invention generally include a plurality of tubes (from a few to a few thousand) arranged at a vertical cross section within an upright column packed with a fixed bed catalyst. These tubes become coked or fouled over time as particulates from the mixed metal oxide catalyst or by products from the gas reaction build up in the reactor. Over time, the reactor becomes clogged and the catalyst becomes too fouled for continued use. In general, a reactant gas feedstock, such as propylene, does not carry any solid particulates or metal-containing species. Rather, high boiling point byproducts and vapor of molybdenum oxides likely condense and deposit in "cold" spots in the reactor, which lead to an abnormal DP increase or pressure drop. As the potential cause of fouling are byproducts formed during oxidation, e.g. of propylene, which typically have boiling point higher than 150° C. at 101.3 kPa (1 atm), and not impurities in the reactant gases, thus selective removal of these high boiling byproducts has not proven as desirable as preventing their formation in the first place. In addition, previously used ceramic materials may not be "inert" enough for fixed bed gas reactor applications as they may increase the formation of high boiling point byproducts. Surprisingly, many so-called inert materials actually contribute to the generation of significant amounts of heavy by-products. The propensity of a material to generate such by-products is not predictable from its activity, or lack thereof, toward major reactants and products.

The present inventors have found that as the run time of a gas phase fixed bed reactor increases, flow restrictions develop at the interstage region in an SRS reactor or at the top of the second catalyst (R2) bed in a tandem reactor. The undesirable by-products and metal oxide vapors likely condense and deposit in these "cold" spots, which then leads to DP increase. Now, in gas phase fixed bed catalyst reactors, such as tandem reactors wherein mixed metal oxide catalysts R1 and R2 are packed in two separate tubes, the present invention provides gaseous oxidation methods by which one can effectively block the formation of by products and hold particulate contaminates in the gaseous mixture or product mixture by including in the reactors an inert macroporous material having a limited surface area. The inert macroporous material of the present invention can be placed anywhere in reactors suited to the oxidation process, such as on the upper stream of a fixed mixed metal oxide catalyst bed. The inert macroporous materials of the present invention behave as filters and hold more particulates than non-porous inerts, such as a Denstone™ 57 media (St. Gobain), which is commonly used in the oxidation process. Surprisingly, the present inventors have discovered that the pressure drop (DP) along the reactor containing inert macroporous material will be maintained low for substantially longer time than the reactor containing non-porous inerts or other inerts not according to the present invention.

In a suitable reactor of the present invention, whether a tandem or single tube reactor, a restriction is located at the interstage region in the SRS reactor or at the top of a second catalyst bed in the tandem reactor where the reaction mixture is cooled down by from 30 to 70° C. from the first tube reactor or first catalyst bed.

In the methods of the present invention, the first bed temperature is greater than the second bed temperature by from 20 to 70° C., or, preferably by by from 30° C. or more.

A wide variety of materials have been proposed for use as inert macroporous materials in reactors and auxiliary equipment. However, suitable inert macroporous materials employed in the present invention result in lower amounts of phthalic acid formed when compared to the use of no such macroporous material. Non-limiting examples of possible inert materials include, for example, porous or nonporous aluminum oxides, such as α-alumina, thorium dioxide, zirconium dioxide, zirconium oxide, titanium oxide, silica, pumice, silicon carbide, silicates such as magnesium silicate, aluminum silicate, steatite, and silica. Organic polymer materials, such as heat resistant polyurethane foams, as well as porous metals that are inert in the gas phase reaction methods of the present invention may be used. Any macroporous material can be tested for inertness, as defined above.

In a process for selecting a macroporous materials for use in gas phase oxidation to produce monomers, one can test to see if the macroporous material is inert, as described above. How inert a macroporous material is relates to the ability of the material to prevent or avoid production of by products.

The process for testing whether a macroporous material is inert\comprises selecting a macroporous material for use in monomer production that generates a product comprising an equal or lower ratio of phthalic acid (PTA) to the total mass of acrolein and acrylic acid product than is generated in the absence of any macroporous material. This can be determined as a $PTA_{inert}$ for each macroporous material, and selecting the macroporous material with an acceptable $PTA_{inert}$ or, preferably, the lowest $PTA_{inert}$.

In the present invention, other heavy byproducts alone or combined can be used in addition to or instead of phthalic acid to evaluate the inertness of a would be inert material. Such heavy byproducts include, for example, benzoic acid, isophthalic acid, terephthalic acid, and benzene-1,2,4-tricarboxylic acid.

Suitable macroporous materials may include, for example, those available as MacroTrap™ XPore 80 material from St. Gobain/NorPro, i.e. Norton Chemical Process Products Corporation (Stow, Ohio). Other suitable macroporous materials having the pore volume, surface area at pore diameter of the present invention may be obtained from Criterion Catalysts and Technologies (Houston, Tex.) as SENTRY™ guard catalysts and supports.

The methods of the present invention are carried out in a reactor under conditions sufficient to produce a desired monomer. Selective oxidation processes for the production of acrylic acid and acrolein, and catalysts for use therein, are well-known to those skilled in the art; see, e.g. US 2013/0274508, to DeCourcy et al., relating to the production of acrylic acid and acrolein, and catalysts for use therein. Similarly, selective oxidation processes for the production of methacrolein and methacrylic acid, and catalysts for use therein, are also well-known to those skilled in the art; see U.S. Pat. Nos. 5,087,744 and 5,532,199, the teachings of which relate to the production of methacrolein and mathacrylic acid, and catalysts for use therein.

The methods of the present invention can be employed for monomers, such as alpha, beta unsaturated carboxylic acids, such as acrylic monomers, for example, (meth)acrylic acid, as well as unsaturated aldehydes, such as (meth)acrolein. Likewise, the oxidation process can comprise the vapor phase oxidation of a compound selected from isobutylene, tert-butanol, and combinations thereof, to methacrolein and methacrylic acid.

The present invention will now be illustrated in detail in the following Examples.

EXAMPLES

Comparative Synthesis Example 1

Propylene oxidation to acrolein and acrylic acid was conducted in two stages. Oxidation of propylene is conducted in a first tube reactor to generate a gaseous mixture similar to the first step in a two-step propylene oxidation process to produce acrylic acid. Then, 15 ml of a mixed metal oxide catalyst R1 available from Nippon Kayaku Co. (Tokyo, Japan) was mixed with 15 ml of 1/8" Denstone™ 57 material beads (Saint-Gobain Norpro, Stow, Ohio), before being loaded into a 2.54 cm (1") outer diameter (OD) stainless steel (SS) first stage tube reactor (0.834" ID). Denstone™ 57 material contains alumina in the range of from 19.0 to 26.0 wt. %, and silica in the range of 64.0 to 75.0 wt. %, with minor components from $Fe_2O_3$, $TiO_2$, CaO, MgO, $Na_2O$, and $K_2O$. Denstone™ 57 material has surface area of less than 1.0 $m^2/g$, and pore volume of less than 0.3 cc/g, with 90% of pore size less than 100 μm. The tube was heated to 367° C. in a clam-shell electrical furnace. The feed to the first stage tube reactor is a mixture of 24.0 ml/min propylene, 211.6 ml/min air, 34.0 ml/min $N_2$, and 1.44 gram/h deionized water. The values of all gas flow rates were adjusted to their would be flow rates under standard temperature (0° C.) and standard pressure (101.3 kPa) conditions. The water was injected by a syringe pump into a SS mixer vessel heated to 180° C. The other feed gases were controlled by mass flow controller. About 100-150 ml of the Denstone™ 57 material was loaded into a separate 2.54 cm OD×45.7 cm long (1" OD×18" long) SS tube, which serves as a second reactor tube residing in a clam-shell electrical furnace. The effluent from the first stage reactor, designated as P1, was fed directly to the inert bed of the second reactor via a 0.63 cm (1/4") SS transfer tube. Both reactors were vertically oriented and in a downflow configuration, i.e., the feed was fed to the top of each reactor.

The product transfer tube between the reactors was heated by heating tape to 260° C. to prevent condensation of the reaction products, especially heavy by-products. The effluent from the first stage reactor or from the second reactor was collected and analyzed periodically. The effluent first flows through a first trap, designated T1, which was cooled by a recirculation chiller at 0-2° C. The gases escaping the first trap flow flowed through a second trap, designated T2, immersed in water/ice, and then through a third trap, designated T3, which was immersed in a dry ice/isopropanol mixture. The trap collection time was 3-4 hours. A 2 wt. % of hydroquinone solution in iso-propanol, or 1000 ppm of phenothiazine in iso-propanol, was used as inhibitor solution. A polymerization inhibitor solution of 6 to 12 grams was injected into each trap before sample collection to prevent polymer formation.

The offgas from T3 was analyzed on-line by a gas chromatograph (GC) equipped with a thermal conductivity detector and a 5 Å molecular sieve/silica gel column. The main gas components in the off gas typically include nitrogen, oxygen, unreacted propylene, carbon monoxide, and carbon dioxide. The liquids collected from T1 and T2 were combined into one sample, labeled as TS-12, before off-line analysis. The liquid collected from T3 was labeled as TS-3. The TS-12 and TS-3 samples were sent for off-line analysis by a gas chromatogram (GC) equipped with flame ionization detector and a capillary column DB-FFAP 123-3232E (Agilent Technologies, USA). The amounts of major products, such as acrylic acid, acrolein, acetaldehyde, acetone, propionic acid, acetic acid were recorded in Table 2, below.

The TS-12 and TS-3 samples were further analyzed for phthalic acid concentration using high performance liquid chromatography (HPLC). The HPLC instrument parameters are provided in Table 1, below.

TABLE 1

| HPLC Instrumental Parameters | |
|---|---|
| Instrument: | Agilent 1200 Series Liquid Chromatograph |
| Column: | Hypersil GOLD PFP (Thermo Scientific) |
| Dimensions: | 4.6 × 250 mm, 5 μm particle size |
| Column Temperature: | 25° C. |
| Injection Volume: | 2 μL |
| Column Flow Rate: | 0.96 mL/min |

| Solvent Composition Timetable: | | % A | % B |
|---|---|---|---|
| Solvent A = MilliQ water with 0.1% phosphoric acid | 0.0 min | 90 | 10 |
| | 16.0 min | 65 | 35 |
| | 22.0 min | 45 | 55 |
| Solvent B = acetonitrile (ACN) | 22.1 min | 90 | 10 |
| | 50.0 min | 90 | 10 |
| | 51.0 min | 90 | 10 |
| Detector: | Diode Array Detector | | |
| Monitor Signal: | 235 nm | | |
| Data Acquisition and Data Analysis: | Agilent ChemStation, version B.03.01 | | |

The phthalic acid standard material was obtained from Sigma-Aldrich (St. louis, Mo.). The initial stock standard solution was prepared in dimethyl sulfoxide (DMSO) solvent at various concentrations between 10-1000 ppm. The working standard solution was prepared by diluting 0.2 g of stock standard in 2 ml of acetonitrile. The working standard solution was filtered with a 0.45 μm syringe filter and delivered to a 2 ml autosampler vial for injection into the HPLC.

The reactor temperature of the first stage reactor was maintained at 367° C. to obtain a gaseous mixture. The composition of the effluent was analyzed by GC and the main components are listed in Table 2, below. The concentration of individual components may vary due to variation in experimental control or catalyst performance.

TABLE 2

| Composition of the Comparative First stage reactor effluent P1 | |
|---|---|
| Component | Mole % |
| $CO_2$ | 0.892 |
| $C_3H_6$ | 0.217 |
| $O_2$ | 5.793 |
| Argon | 0.695 |
| $N_2$ | 67.368 |
| CO | 0.378 |

TABLE 2-continued

Composition of the Comparative First stage reactor effluent P1

| Component | Mole % |
|---|---|
| $H_2O$ | 17.937 |
| Acetaldehyde | 0.073 |
| Acetone | 0.004 |
| Acrolein | 5.929 |
| Acetic Acid | 0.038 |
| Propionic Acid | 0.000 |
| Acrylic Acid | 0.676 |

The propylene conversion, yield of acrolein and acrylic acid, and relative amount of pthalic acid are calculated according to the equations below.

Propylene conversion (%)=(moles of propylene fed–moles of propylene unreacted)/moles of propylene fed.

Yield of acrolein & Acrylic Acid (%)=(moles of acrolein formed+moles of AA formed)/moles of propylene fed.

The relative total amount of phthalic acid from TS-12 and TS-3 samples verses the total amount of acrolein and AA formed is calculated according to the equations below:

$PTA_{inert}$(ppm)=(mass of phthalic acid in TS-12 and TS-3 samples with inert loaded in second reactor tube)/(total mass of acrolein and AA in TS-12 and TS-3 samples with inert loaded in second reactor tube)*1,000,000.

Comparative Example 1A

Inertness of Denstone™ 57 Material in a Second Stage Reaction

The off gas analysis from Comparative Synthesis Example 1, above, was conducted with 100 ml of Denstone™ 57 material 6.4 mm (¼") spheres (Saint Gobain Norpro), loaded into a second stage reactor tube. The contact time of Denstone™ 57 material with the effluent from the first stage reactor in Comparative Synthesis Example 1 was 20 seconds. The effluents from the second stage reactor were collected as described above and analyzed. The temperature of the second stage reactor was controlled at from 270 to 320° C. The resulting propylene conversion, yield of "acrolein and AA," and phthalic acid are listed in Table 3, below. The data at 320° C. was the average of two samples.

Example 2

Inertness of MacroTrap™ XPore 80 Macroporous Material

The off gas analysis from Comparative Example 1, above, was conducted with 110 ml of MacroTrap™ XPore 80 media 10 mm rings (Saint Gobain Norpro), loaded in the top of a second stage reactor tube. MacroTrap™ XPore 80 material 10 mm rings contain alumina in the range of 60 to 100 wt. %, and silica in the range of 0 to 40 wt. %. MacroTrap™ XPore 80 media 10 mm rings have surface area less than 0.25 m²/g, and a 0.40 to 0.60 cc/g pore volume, with from 0.2 to 0.35 cc/g having with pore size larger than 100 μm. The contact time of the MacroTrap™ XPore 80 material with the effluent from the first stage reactor in Comparative Synthesis Example 1, was 22 seconds. The effluents from the second stage reactor were collected as described above and analyzed. The second stage reactor was controlled at from 270 to 320° C. The propylene conversion, yield of "acrolein and AA," and phthalic acid are listed in Table 3, below. The data at 320° C. is the average of three samples.

Comparative Example 3

Inertness of MacroTrap™ Media 1.5 Material

The off gas analysis from the above Comparative Example 1 was conducted with 120 ml of MacroTrap™ Media 1.5 material as 6 mm spheres (Saint Gobain Norpro), loaded in the second stage reactor tube. MacroTrap™ Media 1.5 material contains alumina in the range of 90 to 100 wt. %, and silica in the range of 0 to 10 wt. %. MacroTrap™ Media 1.5 material has surface area more than 1.50 m²/g, and from 0.15 to 0.30 cc/g pore volume having a pore size larger than 100 μm. The contact time of the MacroTrap™ Media 1.5 material with the effluent from the first stage reactor in Comparative Synthesis Example 1 was 24 seconds. The effluents from second stage reactor were collected as described above and analyzed. The temperature of the second stage reactor was controlled at 270 and 320° C. The propylene conversion, yield of "acrolein and AA," and phthalic acid are listed in Table 3, below. The data at 320° C. is the average of two samples.

TABLE 3

Change of Reactant Conversion, Product Yield, and Heavy By-product Formation with Various Inert Materials

| Example | Material tested | Temperature of 2$^{nd}$ reactor (° C.) | PP Conv. (%) | Yield of "acrolein + AA" (%) | PTA (ppm vs. combined acrolein and AA) |
|---|---|---|---|---|---|
| Comp. 1A | Denstone ™ 57 media | 270 | 97.2 | 90.6 | 86 |
|  |  | 320 | 97.0 | 91.4 | 73.5 |
| 2 | macroporous material (MacroTrap ™ XPore 80) | 270 | 96.8 | 91.3 | 83 |
|  |  | 320 | 96.8 | 90.3 | 70 |
| Comp. 3 | MacroTrap ™ Media 1.5 material | 270 | 96.0 | 93.0 | 147 |
|  |  | 320 | 96.3 | 92.0 | 111 |

The results in Table 3, above, show that the combined yield of "acrolein and AA" is comparable among the three materials tested, when accounting for experimental error. Surprisingly, the inventive macroporous material of Example 2 MacroTrap™ XPore 80 yields a much lower amount of PTA (ppm) than the MacroTrap™ Media 1.5 material in Comparative Example 3.

Example 5

Evaluation Macroporous Material as Overlay on Second Stage Catalyst Bed

The indicated materials were placed in a 30 cm (12") long pre-heating zone that sits right above a second stage catalyst bed in a tandem reactor in which propylene is oxidized into acrolein in the first stage reactor. The acrolein is oxidized into acrylic acid in the second stage reactor. Both the reactors are shell and tube tubular reactors with tubes packed into a cross-sectional area of the tubular reactor, and with catalyst packed in the tubes and heat transfer media circulating between the tubes.

During the scheduled replacement of the overlay inert material bed placed on the top of second stage catalyst, a full row of the tubes with 2.4 cm (0.96") ID were filled with the macroporous material of Example 2 as 6 mm rings, or the media of Comparative Example 3 as 6 mm rings, with the majority of the tubes filled with the Denstone™ 57 material as 6.4 mm (¼") spheres. The pressure drop (DP) of the catalyst bed both without the loading of the overlay bed was measured one tube at a time using an air pressure test wand to measure air pressure at the top of the tested tube and to measure the resistance flowing through each tube with a desired flow of air at 45 SLPM (Standard Liter per Minute) flowing into the top of the tested tube. A pressure transmitter measured the DP across a loaded reactor tube (with the other end of the reactor tube open to the atmosphere). The reaction was resumed after the overlay replacement was completed. The reaction was stopped about 5 months later. The reactor was opened and the pressure drop of the tubes after the tested overlay material was removed. The pressure drop data are summarized in Table 4, below.

TABLE 4

Change of DP for the tubes packed with different overlay materials

| Overlay material in the tube | Number of tubes with DP measured | Average DP (psi) Initial | Average DP (psi) Final | DP increase (%) |
|---|---|---|---|---|
| Example 2 | 93 | 10.09 | 10.69 | 5.95 |
| C. Ex. 1A | 88 | 10.06 | 10.85 | 7.85 |
| C. Ex. 3 | 93 | 9.70 | 10.38 | 7.01 |

All the packed tubes had a pressure increase over the 5 months of operation. However, the percentage of DP increase was the smallest in the tubes packed with an inert macroporous material of Example 2, while the highest in the tubes packed with non-porous Denstone™57 media.

The tubes packed with the media of Comparative Example 3 had relatively smaller DP increase compared to the tubes packed with the material of Comparative Example 1A.

I claim:

1. A method for preparing monomers having an alpha, beta-unsaturated carboxylic acid comprising oxidizing one or more reactant gases selected from propylene, isobutylene, and tert-butanol in a fixed bed reactor in the presence of oxygen and a mixed metal oxide catalyst to form an oxidized gaseous mixture and, at any point in the oxidizing, feeding or flowing the one or more reactant gases or the oxidized gaseous mixture through an inert macroporous material that has a pore volume of from 0.2 cm$^3$/g to 2.0 cm$^3$/g, a surface area of from 0.01 to 0.6 m$^2$/g, and wherein from 30 to 98 wt. % of the total pore volume in the inert macroporous material has a pore diameter of at least 100 μm.

2. The method as claimed in claim 1, wherein the oxidizing is conducted in two stages starting with a first stage in a first reactor containing at least one bed containing in the bed a first mixed metal oxide catalyst R1 to generate a gaseous mixture and then a second stage in a second reactor containing at least one bed containing in the bed a second mixed metal oxide catalyst R2 to generate a product comprising a monomer.

3. The method as claimed in claim 2 wherein the bed temperature of the second stage catalyst bed is from 250 to 380° C.

4. The method as claimed in claim 1 wherein the oxidation process is vapor phase oxidation of propylene to acrolein and acrylic acid.

5. The method as claimed in claim 1 wherein the oxidation process is the vapor phase oxidation of isobutene and/or tert-butanol to methacrolein and methacrylic acid.

6. The method as claimed in claim 1 wherein the mixed metal oxide catalyst contains Mo and Bi.

7. The method as claimed in claim 1, wherein the macroporous material is chosen from a silicon oxide, an aluminum oxide, a zirconium oxide, a germanium oxide, mixtures thereof and combinations thereof.

8. The method as claimed in claim 1, wherein in the oxidizing the one or more reactant gas is propylene gas and is oxidized to an acrolein containing gaseous mixture by feeding the propylene gas from the upper stream of a first stage catalyst bed containing in the bed a solid first mixed metal oxide catalyst R1 at a first temperature, and then the resulting acrolein gaseous mixture is oxidized to an acrylic acid product by feeding the acrolein gaseous mixture from the upper stream of a second stage catalyst bed containing in the bed a solid second mixed metal oxide catalyst R2 at a second temperature, wherein the improvement comprises including the macroporous material in at least one of the upper stream of the first stage catalyst bed, the upper stream of the second stage catalyst bed, the bottom stream of the first stage catalyst bed, and the bottom stream of the second stage catalyst bed.

9. The method as claimed in claim 1, wherein the one or more reactant gases are oxidized in at least one first stage catalyst bed in a first tube reactor having a bed containing a solid first mixed metal oxide catalyst R1 at a first temperature, and then the resulting gaseous mixture is oxidized to a monomer product by feeding the gaseous mixture to the upper stream of a second tube reactor having at least one catalyst bed containing a solid second mixed metal oxide catalyst R2 at a second temperature, wherein the improvement comprises including the macroporous material in at the bottom of a first tube reactor, at the interstage region between the first tube reactor and the second tube reactor, top of the second tube reactor, or the bottom of second tube reactor.

10. The method as claimed in claim 1, wherein the alpha, beta-unsaturated carboxylic acid is selected from the group consisting of acrylic acid and methacrylic acid.

11. The method as claimed in claim 10, wherein the alpha, beta-unsaturated carboxylic acid is acrylic acid.

12. The method as claimed in claim 10, wherein the alpha, beta-unsaturated carboxylic acid is methacrylic acid.

* * * * *